(12) United States Patent
Lois

(10) Patent No.: US 11,577,046 B2
(45) Date of Patent: Feb. 14, 2023

(54) U SLEEP WEIGHTED PILLOW

(71) Applicant: Eric Lois, Muskego, WI (US)

(72) Inventor: Eric Lois, Muskego, WI (US)

(*) Notice: Subject to any disclaimer, the term of this patent is extended or adjusted under 35 U.S.C. 154(b) by 0 days.

(21) Appl. No.: 16/679,194

(22) Filed: Nov. 9, 2019

(65) Prior Publication Data
US 2021/0138184 A1    May 13, 2021

(51) Int. Cl.
*A61M 21/00* (2006.01)
*A61M 21/02* (2006.01)
*A61F 7/02* (2006.01)
*A61F 7/00* (2006.01)

(52) U.S. Cl.
CPC ........... *A61M 21/02* (2013.01); *A61F 7/02* (2013.01); *A61F 2007/0002* (2013.01); *A61F 2007/0004* (2013.01); *A61F 2007/0242* (2013.01); *A61F 2007/0261* (2013.01); *A61M 2021/0016* (2013.01); *A61M 2021/0066* (2013.01); *A61M 2210/06* (2013.01)

(58) Field of Classification Search
CPC .......... A61M 21/02; A61M 2021/0016; A61M 2021/0066; A61M 2210/06; A61F 7/02; A61F 2007/0004; A61F 2007/0242; A61F 2007/0261; A61F 2007/0002; A61F 7/0241; A61F 7/00; A61F 7/0097; A47G 9/10; A47G 9/1036
See application file for complete search history.

(56) References Cited

U.S. PATENT DOCUMENTS

| | | | |
|---|---|---|---|
| 8,468,628 B1 | 6/2013 | Cheng | |
| 9,462,902 B1* | 10/2016 | Rukel | A47G 9/10 |
| 2004/0243203 A1* | 12/2004 | Lavine | A61F 7/02 607/114 |
| 2009/0126117 A1* | 5/2009 | Lazarus | A47G 9/0253 5/644 |
| 2010/0217363 A1* | 8/2010 | Whitely | A61F 7/02 607/112 |
| 2012/0272453 A1* | 11/2012 | Jaskot | A47G 9/10 5/644 |
| 2013/0263377 A1* | 10/2013 | Wootten, Jr. | A47C 27/15 5/640 |
| 2015/0351956 A1* | 12/2015 | Enderby | A61F 7/08 607/108 |
| 2018/0193512 A1 | 7/2018 | Antonino | |
| 2019/0298089 A1* | 10/2019 | Abdul | A47G 9/1027 |
| 2019/0343307 A1* | 11/2019 | Cullins | A47G 9/1036 |
| 2020/0405999 A1* | 12/2020 | Goodstadt | A47C 31/005 |

* cited by examiner

*Primary Examiner* — Kaylee R Wilson

(57) ABSTRACT

A U sleep weighted pillow promotes healthy sleep essential oils is presented. The U sleep weighted pillow provides comfort to a head, to an upper portion of the face, for body aches and pains. The U sleep weighted pillow provides a warming or a cooling to a desired body part while a person is laying down, sitting, etc. The U sleep weighted pillow further has custom weighting and firmness of the U sleep weighted pillow by the person. The U sleep weighted pillow helps restore movement from injured tissue, reduces joint stiffness, muscle spasms, sprains, strains, whiplash, pain relief, ease pain from both acute and chronic injuries, arthritis, promotes blood circulation and helps to relax muscle.

8 Claims, 3 Drawing Sheets

U SLEEP WEIGHTED PILLOW

FIELD OF THE INVENTION

This invention relates to sleeping pillows. More particularly, it relates to sleeping pillows having therapeutic attributes.

BACKGROUND

A pillow is a support of the body at rest for comfort, therapy, or decoration. Pillows are used by many species, including humans. Some types of pillows include throw pillows, body pillows, decorative pillows and many more. Pillows that aid sleeping are a form of bedding that supports the head and neck. Other types of pillows are designed to support the body when lying down or sitting. There are also pillows that consider human body shape for increased comfort during sleep. Decorative pillows used on beds, couches or chairs are sometimes referred to as cushions.

In contemporary western culture, pillows consist of a plain or patterned fabric envelope (known as a pillowcase) which contains a soft stuffing, typically synthetic and typically standardized in sizes and shape. Pillows have been historically made of a variety of natural materials and many cultures continue to use pillows made from natural materials in the world.

An essential oil is a concentrated hydrophobic liquid containing volatile (easily evaporated at normal temperatures) chemical compounds from plants. Essential oils are also known as volatile oils, ethereal oils, aethereal, or simply as the oil of the plant from which they were extracted, such as oil of clove. An essential oil is "essential" in the sense that it contains the "essence of" the plant's fragrance—the characteristic fragrance of the plant from which it is derived. The term "essential" used here does not mean indispensable, as with the term's essential amino acid or essential fatty acid, which are so called because they are nutritionally required by a given living organism. In contrast to fatty oils, essential oils typically evaporate completely without leaving a stain or residue.

Essential oils are generally extracted by distillation, often by using steam. Other processes include expression, solvent extraction, Pfumatra, absolute oil extraction, resin tapping, wax embedding, and cold pressing. They are used in perfumes, cosmetics, soaps and other products, for flavoring food and drink, and for adding scents to incense and household cleaning products.

Essential oils are often used for aromatherapy, a form of alternative medicine in which healing effects are ascribed to aromatic compounds. Aromatherapy may be useful to induce relaxation, but there is not sufficient evidence that essential oils can effectively treat any condition. Improper use of essential oils may cause harm including allergic reactions and skin irritation, and children may be particularly susceptible to the toxic effects of improper use.

People are exhausted these days. Insomnia is at epidemic levels where stress, anxiety and worries are the major components. According to the CDC, 1 in 4 adults don't get enough sleep; 7-9 hours is optimal amount of sleep. At least 40 million Americans are diagnosed with chronic, long-term sleep disorders each year. Studies reveal that not only zolpidem (commonly found in medicines such as Ambien®) bad for your health but also ineffective. Sleeping less than 7-8 hours a night is linked to an increased risk of heart disease and stroke.

Accordingly, and in light of the foregoing, there is a need for a pillow that helps to promote good, healthy sleep. It would further be beneficial that the pillow has an ability to apply essential oils while the person is sleeping.

DETAILED DESCRIPTION

Figure 1:
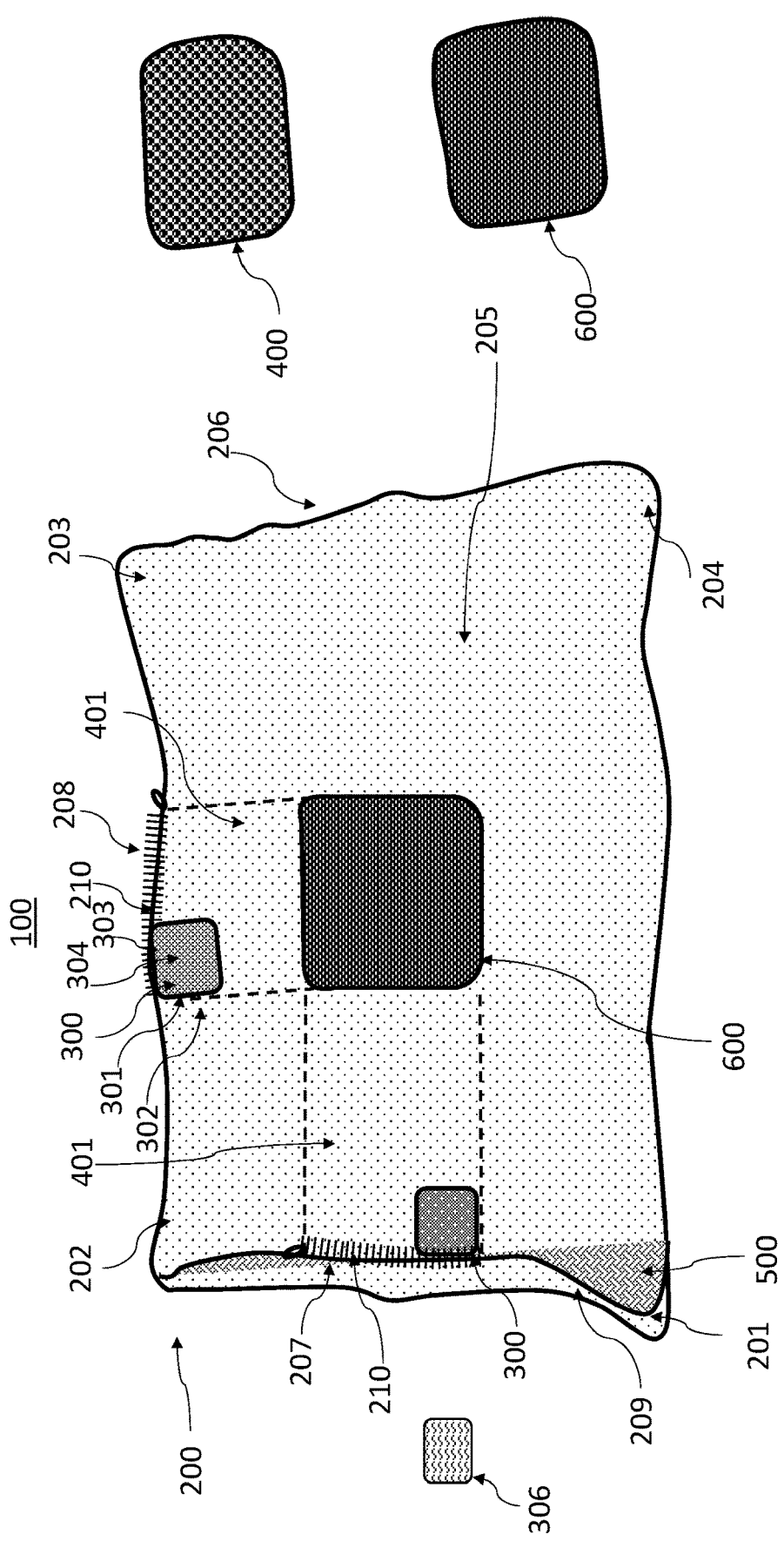
FIG. 1A is an illustrated view of an exemplary U sleep weighted pillow.
FIG. 1B is an illustrated view of a bladder for use in the exemplary U sleep weighted pillow shown in FIG. 1A.

The phrases "in one embodiment," "in various embodiments," "in some embodiments," and the like are used repeatedly. Such phrases do not necessarily refer to the same embodiment. The terms "comprising," "having," and "including" are synonymous, unless the context dictates otherwise. Such terms do not generally signify a closed list.

"Above," "adhesive," "affixing," "any," "around," "both," "bottom," "by," "comprising," "consistent," "customized," "enclosing," "friction," "in," "labeled," "lower," "magnetic," "marked," "new," "nominal," "not," "of," "other," "outside," "outwardly," "particular," "permanently," "preventing," "raised," "respectively," "reversibly," "round," "square," "substantial," "supporting," "surrounded," "surrounding," "threaded," "to," "top," "using," "wherein," "with," or other such descriptors herein are used in their normal yes-or-no sense, not as terms of degree, unless context dictates otherwise.

Reference is now made in detail to the description of the embodiments as illustrated in the drawings. While embodiments are described in connection with the drawings and related descriptions, there is no intent to limit the scope to the embodiments disclosed herein. On the contrary, the intent is to cover all alternatives, modifications and equivalents. In alternate embodiments, additional devices, or combinations of illustrated devices, may be added to, or combined, without limiting the scope to the embodiments disclosed herein.

Referring to FIG. 1A and FIG. 1B, an illustrated view of an exemplary U sleep weighted pillow 100 for promoting healthy sleep and healing therapy is presented. The U sleep weighted pillow 100 is useful for providing comfort to a head, upper face, body aches and pains. The U sleep weighted pillow 100 is also useable for providing a warming or a cooling to a desired body part, such as a person's head and eyes, while the person is laying down, sitting, etc. The U sleep weighted pillow 100 further is useful providing a custom weighting and firmness of the U sleep weighted pillow 100 by the person. The U sleep weighted pillow 100 is useful in helping a person through heat/cool therapy, essential oils and weighting of the U sleep weighted pill 100 to have healthy sleep and further is useful in restoring movement from injured tissue, reduces joint stiffness, muscle spasms, sprains, strains, whiplash, pain relief, ease pain from both acute and chronic injuries, arthritis, promotes blood circulation and helps to relax muscle. A primary use of the U sleep weighted pillow 100 is for a head and face of a person promoting healthy sleep; however, the U sleep weighted pillow 100 is also useful for other parts of the body to promote healing.

The U sleep weighted pillow 100 has a pillow 200, a pocket 300, one or more bladders 400, 600 and a stuffing 500.

The pillow 200 preferably has a length of between sixteen and eighteen (16-18) inches, however other lengths are hereby contemplated, including, but not limited to, fifteen (15) inches, twenty (20) inches, etc. The pillow 200 preferably has a width of between twelve and fourteen (12-14) inches, however other widths are hereby contemplated, including, but not limited to, eleven (11) inches, fifteen (15) inches, etc. The pillow 200 preferably has a height of between one and three (1-3) inches, however other heights are hereby contemplated, including, but not limited to, one-half (0.5) inch, four (4) inches, etc. The pillow 200 is preferably hypo-allogenic. The pillow 200 is preferably made of natural material such as cotton, silk, etc. The pillow 200 is preferably a rectangular shape, however other shapes are hereby contemplated, including, but not limited to, round, square, etc. The pillow 200 is pliable and shapeable.

The pillow 200 has a plurality of corners 201, 202, 203, 204, a front 205, a back 206, one or more openings 207, 208 and an inside 209. The inside 209 of the pillow 200 is preferably hollow. The first of the openings 207 is substantially half way between the first of the plurality of corners 201 and the second of the plurality of corners 202. The second of the openings 208 is substantially half way between the second of the plurality of corners 202 and the third of the plurality of corners 203. Although two openings are presented, any number of openings, including only a single opening, are contemplated.

The front 205 of the pillow is preferably made of a plush, comfortable material. The back 206 of the pillow 200 is preferably made of a microfiber, moisture wicking, cooling material.

Each of the one or more openings 207, 208 have a closure 210. The closure 210 is preferably a zipper, however other types of closures are hereby contemplated, including, but not limited to, tongue and groove, snaps, etc.

The stuffing 500 is removably coupled to the inside 209 of the pillow 200. To access, the stuffing 500, the closure 210 of the first of the openings 207 is opened. The stuffing 500 is removed to attain a desired weight. The closure 210 is then secured closed to retain the stuffing 500 in the inside 209 of the pillow 200. The stuffing 500 is preferably a malleable weight stuffing material. The stuffing 500 may be placed over a face 903 (see FIG. 2) or head where it is useful for blocking out ambient light and noise. The stuffing 500 of the pillow 200 preferably has a weight of between one and three (1-3) pounds, however other weights are hereby contemplated, including, but not limited to, one-half (0.5) pound, four (4) pounds, etc. The preferred weight of the stuffing 500 can help calm the mind, gives a secure feeling and a body a cue to rest.

Shown in FIG. 1B, the bladder 400 is a heat keeping bladder. The bladder 400 is heated to a desired temperature by placing the bladder in a microwave oven or similar type of device. The bladder 400 preferably has a heat-retaining material filling such as a rice-based filling. The bladder 400 may also be kept at room temperature.

Shown in FIG. 1B, the bladder 600 is a cold keeping bladder. The bladder 400 is cooled to a desired temperature by placing the bladder in a freezer, refrigerator or similar device. The cold bladder 600 preferably has a cooling-material filling. The bladder 600 may also be kept at room temperature.

The bladder 400, 600 may be placed in a sleeve 401. The sleeve 401 allows for the bladder 400, 600 to remain in a single place on the inside 209 of the pillow 200. The bladder 400, 600, whether in the sleeve 401 or not, is then placed through one of the openings 210 of the pillow 200 into a desired location within the inside 209 of the pillow 200.

The pocket 300 has a front 301, a back 302 and an opening 303. The opening 303 of the pocket 300 allows for access to an inside 304 of the pocket 300. The inside 304 of the pocket 300 is preferably waterproof. The pocket 300 is coupled to the front 201 of the pillow 200 substantially near the opening 207, 208. The opening 303 of the pocket 200 allows for an essential oil packet 306 to be stored.

The essential oil packet 306 are placed into the inside 306 of the pocket 300. The opening 303 of the pocket 200 allows for the dispersion of the essential oil from the essential oil packet 306. The essential oils can be any of the essential oils being sold, including, but not limited to, Lavender, Peppermint, Eucalyptus, Frankincense, Chamomile, etc.

Figure 2:
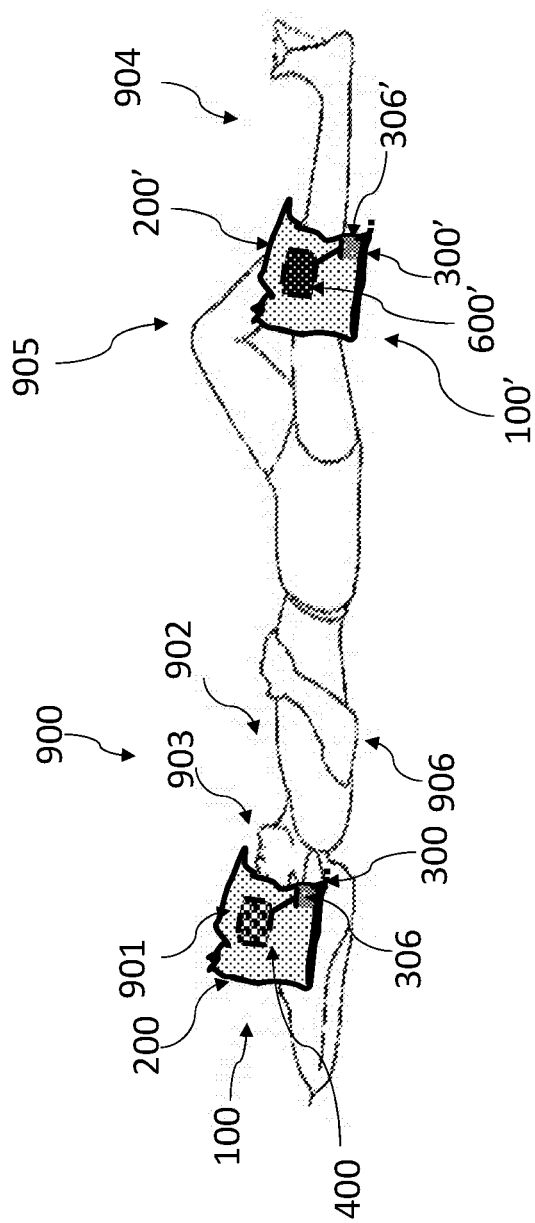
FIG. 2 is an illustrated view of a use of the U sleep weighted pillow shown in FIG. 1A.

Moving now to FIG. 2, an illustrated view of a use of the U sleep weighted pillow 100 shown in FIG. 1A is presented.

A person 900 determines a desired position to lay in. The person 900 has a head 901, a torso 902, a face 903, a plurality of legs 904, a plurality of knees 905 and a plurality of arms 906. The U sleep weighted pillow 100 may be placed around the head 901, over the face 903, or anywhere else desired.

The person 900 determines where they desire to place the U sleep weighted pillow 100. The pockets 300 have the essential oils 306 and the bladder 400 is chosen and heated to a desired temperature in a microwave oven or if the cold bladder 600 is chosen, the cold bladder 600 would be cooled to a desired temperature in a refrigerator or freezer. The bladder 400 is inserted into the pillow 200. The person 900 places the U sleep weighted pillow 100 where the bladder 400 can disperse heat, room temperature or cold and essential oils while being applied to the head 901.

Further, a second U sleep weighted pillow 100' may be used to be placed over another portion of the person 900. The pockets 300' have the essential oils 306' and the cold bladder 600' is chosen and cooled to a desired temperature in a freezer or refrigerator. The bladder 600' is inserted into the pillow 200'. The person 900 places the second U sleep weighted pillow 100' where the bladder 600' can disperse heat, room temperature or cold and essential oils while being applied to the head 901.

Figure 3:
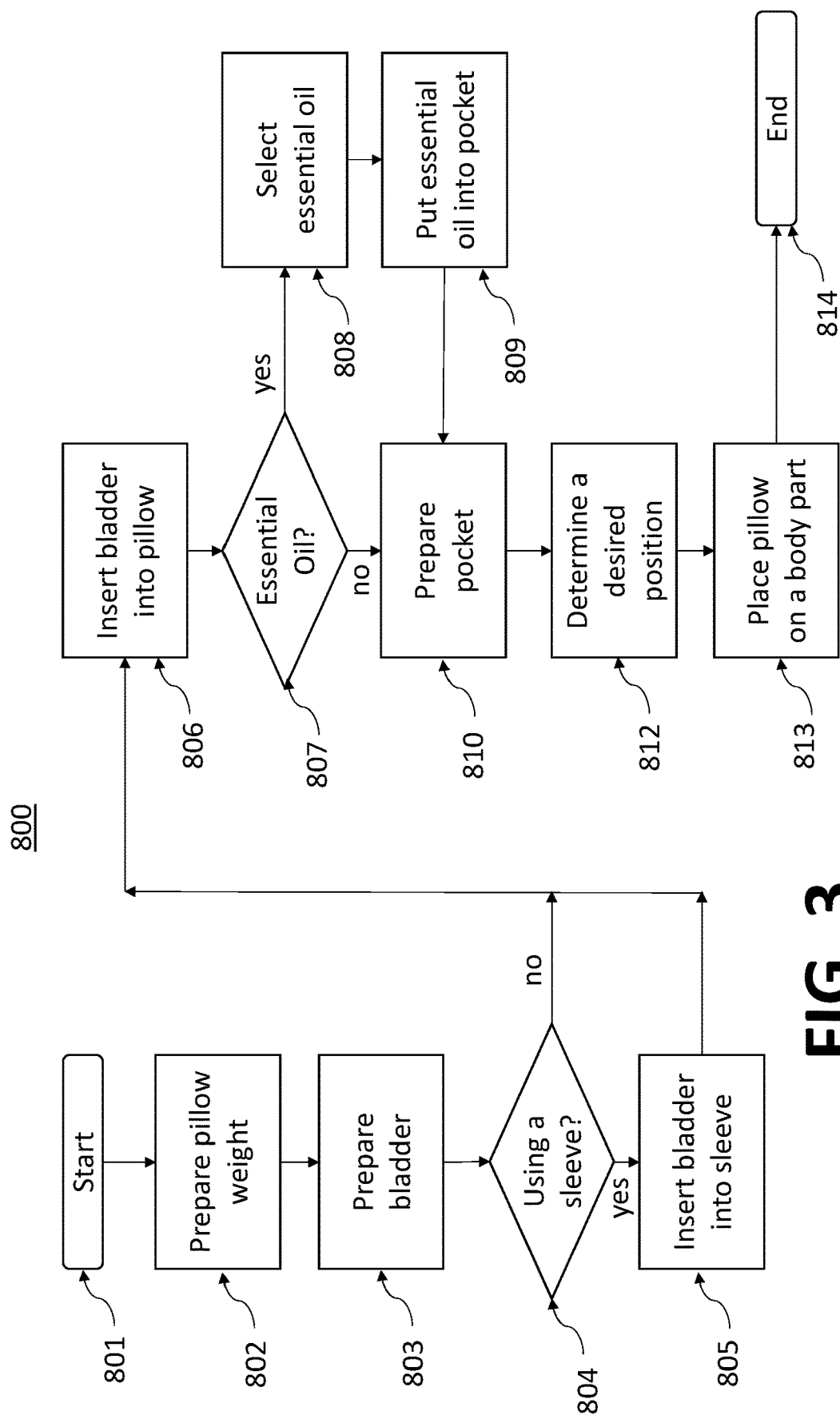
FIG. 3 is a flowchart of a use of the U sleep weighted pillow shown in FIG. 1A.

Referring now to FIG. 3, a flowchart 800 for a utilizing the U sleep weighted pillow 100 shown in FIG. 1A is presented.

The flowchart 800 being at the start 801. At 802, the person 900 prepares the pillow weight by first determining the desired weight of the pillow 200. The person 900 then opens the pillow 200 to access the stuffing 500 on the inside of the pillow 200. The person 900 removes stuffing 500 if the desired weight is less than the current weight of the pillow 200 or insert more stuffing 500 into the pillow 200 if the desired weight is greater than the current weight.

At 803, the person 900 prepares the bladder 400, 600. The person 900 determines the desired temperature and then selects either bladder 400 to heat or bladder 600 to cool. If the person 900 desires room temperature, either of the bladder 400 or the bladder 600 can be chosen. At 804 if a sleeve is to be used, then at 805 the bladder 400, 600 is inserted into the sleeve 401.

At 806, whether the bladder 400, 600 has been inserted into a sleeve or not, the bladder 400, 600 is inserted into the pillow 200 through one of the openings 207, 208.

At 807, the person 900 determines if an essential oil is to be used and, at 808, if so which of the essential oil packets 306 is desired. At 809, the essential oil packet 306 is placed into the pocket 300. Then at 810, whether essential oil 306 was desired or not, the pocket 300 is coupled to the front 201 of the pillow 200 substantially near one of the openings 207, 208.

At 812, the person 900 then determines a desired relaxing or laying position and lays down. The person 900 also determines which body part is subject to healing. At 813, the person 900 places the U sleep weighted pillow 100 onto the determined body part. At 814, the process ends.

In the numbered clauses below, specific combinations of aspects and embodiments are articulated in a shorthand form such that (1) according to respective embodiments, for each instance in which a "component" or other such identifiers appear to be introduced (with "a" or "an," e.g.) more than once in a given chain of clauses, such designations may either identify the same entity or distinct entities; and (2) what might be called "dependent" clauses below may or may not incorporate, in respective embodiments, the features of "independent" clauses to which they refer or other features described above.

Those skilled in the art will appreciate that the foregoing specific exemplary processes and/or devices and/or technologies are representative of more general processes and/or devices and/or technologies taught elsewhere herein, such as in the claims filed herewith and/or elsewhere in the present application.

The features described with respect to one embodiment may be applied to other embodiments or combined with or interchanged with the features of other embodiments, as appropriate, without departing from the scope of the present invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for promoting healthy sleep, the method comprising:
    preparing a weighted pillow to be a desirable weight by removing stuffing through an opening of the weighted pillow;
    preparing a bladder;
    inserting the bladder into a sleeve;
    inserting the sleeved bladder into a body of the weighted pillow;
    selecting an essential oil;
    preparing a pocket by placing the selected essential oil in the pocket;
    determining a desired position of the weighted pillow on a desired part of the body; and
    placing the weighted pillow on the desired part of the body.

2. The method of claim 1, wherein the preparing the bladder comprising:
    determining a desired temperature of the bladder; and
    heating or cooling the bladder to the desired temperature.

3. The method of claim 1, the bladder being a heat-able bladder.

4. The method of claim 1, the weighted pillow having a length being between sixteen and eighteen (16-18) inches.

5. The method of claim 1, the weighted pillow having a width being between twelve and fourteen (12-14) inches.

6. The method of claim 1, the weighted pillow having a height being between one and three (1-3) inches.

7. The method of claim 1, the essential oil being one of: lavender, peppermint, eucalyptus, frankincense and chamomile.

8. The method of claim 1, the stuffing being made of a malleable weighted material.

* * * * *